United States Patent
Chang et al.

(10) Patent No.: US 8,563,518 B2
(45) Date of Patent: *Oct. 22, 2013

(54) CYCLOSPORIN COMPOSITIONS

(75) Inventors: James N. Chang, Newport Beach, CA (US); Orest Olejnik, Coto De Caza, CA (US); Bruce A. Firestone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/536,479

(22) Filed: Jun. 28, 2012

(65) Prior Publication Data

US 2012/0270805 A1 Oct. 25, 2012

Related U.S. Application Data

(60) Continuation of application No. 11/857,223, filed on Sep. 18, 2007, now Pat. No. 8,211,855, which is a division of application No. 11/255,821, filed on Oct. 19, 2005, now Pat. No. 7,288,520, which is a continuation-in-part of application No. 11/181,409, filed on Jul. 13, 2005, now abandoned.

(51) Int. Cl.
*A61K 38/13* (2006.01)
*A61K 38/12* (2006.01)
*A61K 9/36* (2006.01)
*A61K 31/175* (2006.01)

(52) U.S. Cl.
USPC ............ 514/20.5; 514/21.1; 514/57; 424/480

(58) Field of Classification Search
None
See application file for complete search history.

(56) References Cited

U.S. PATENT DOCUMENTS

| | | |
|---|---|---|
| 4,388,307 A | 6/1983 | Cavanak |
| 4,649,047 A | 3/1987 | Kaswan |
| 4,814,323 A | 3/1989 | Andrieu et al. |
| 4,839,342 A | 6/1989 | Kaswan |
| 4,996,193 A | 2/1991 | Hewitt et al. |
| 5,047,396 A | 9/1991 | Orban et al. |
| 5,051,402 A | 9/1991 | Kurihara et al. |
| 5,342,625 A | 8/1994 | Hauer et al. |
| 5,474,979 A * | 12/1995 | Ding et al. .................. 514/20.5 |
| 5,543,393 A | 8/1996 | Kim et al. |
| 5,614,491 A | 3/1997 | Walch et al. |
| 5,639,724 A | 6/1997 | Cavanak |
| 5,652,212 A | 7/1997 | Cavanak et al. |
| 5,759,997 A | 6/1998 | Cavanak |
| 5,766,629 A | 6/1998 | Cho et al. |
| 5,798,333 A | 8/1998 | Sherman |
| 5,827,822 A | 10/1998 | Floc'h et al. |
| 5,834,017 A | 11/1998 | Cho et al. |
| 5,891,846 A * | 4/1999 | Ishida et al. ............... 514/20.5 |
| 5,916,589 A | 6/1999 | Hauer et al. |
| 5,929,030 A | 7/1999 | Hamied et al. |
| 5,951,971 A | 9/1999 | Kawashima et al. |
| 5,962,014 A | 10/1999 | Hauer et al. |
| 5,962,017 A | 10/1999 | Hauer et al. |
| 5,962,019 A | 10/1999 | Cho et al. |
| 5,977,066 A | 11/1999 | Cavanak |
| 6,007,840 A | 12/1999 | Hauer et al. |
| 6,024,978 A | 2/2000 | Hauer et al. |
| 6,057,289 A | 5/2000 | Mulye |
| 6,197,335 B1 | 3/2001 | Sherman |
| 6,254,860 B1 | 7/2001 | Garst |
| 6,254,885 B1 | 7/2001 | Cho et al. |
| 6,267,985 B1 | 7/2001 | Chen et al. |
| 6,284,268 B1 | 9/2001 | Mishra et al. |
| 6,294,192 B1 | 9/2001 | Patel et al. |
| 6,306,825 B1 | 10/2001 | Cavanak |
| 6,350,442 B2 | 2/2002 | Garst |
| 6,468,968 B2 | 10/2002 | Cavanak et al. |
| 6,475,519 B1 | 11/2002 | Meinzer et al. |
| 6,486,124 B2 | 11/2002 | Olbrich et al. |
| 6,569,463 B2 | 5/2003 | Patel et al. |
| 6,582,718 B2 | 6/2003 | Kawashima et al. |
| 6,638,522 B1 | 10/2003 | Mulye |
| 6,656,504 B1 | 12/2003 | Bosch et al. |
| 6,723,339 B2 | 4/2004 | Meinzer et al. |

(Continued)

FOREIGN PATENT DOCUMENTS

| | | |
|---|---|---|
| EP | 0471293 | 2/1992 |
| WO | WO 00/00179 | 1/2000 |

OTHER PUBLICATIONS

Kuwano et al, "Cyclosporine a Formulation Affects Its Ocular Distribution in Rabbits", Pharmaceutical Research, vol. 19, No. 1, Jan. 2002, 108-111.

(Continued)

*Primary Examiner* — Satyanarayana R Gudibande
(74) *Attorney, Agent, or Firm* — Laura L. Wine; Allergan, Inc.

(57) ABSTRACT

A composition is disclosed herein comprising from about 0.001% to about 0.4% cyclosporin A, castor oil, and a surfactant selected from the group consisting of alcohol ethoxylates, alcohols, alkyl glycosides, alkyl polyglycosides, alkylphenol ethoxylates, amine oxides, block polymers, carboxylated alcohol or alkylphenol ethoxylates, carboxylic acids/fatty acids, cellulose derivatives, ethoxylated alcohols, ethoxylated alkylphenols, ethoxylated aryl phenols, ethoxylated fatty acids, ethoxylated fatty acids, ethoxylated fatty esters and oils, fatty alcohols, fatty esters, glycol esters, lanolin-based derivatives, lecithin and lecithin derivatives, lignin and lignin derivatives, methyl esters, monoglycerides and derivatives, phosphalipids, polyacrylic acids, polyethylene glycols, polyethylene oxide-polypropylene oxide copolymers, polyethylene oxides, polymeric surfactants, polypropylene oxides, propoxylated alcohols, propoxylated alkyl phenols, propoxylated fatty acids, protein-based surfactants, sarcosine derivatives, silicone-based surfactants, sorbitan derivatives, stearates, sucrose and glucose esters and derivatives, and combinations thereof.

1 Claim, No Drawings

(56) References Cited

U.S. PATENT DOCUMENTS

| | | |
|---|---|---|
| 6,916,785 B2 | 7/2005 | Patel |
| 7,202,209 B2 | 4/2007 | Chang et al. |
| 7,288,520 B2 | 10/2007 | Chang et al. |
| 7,501,393 B2 | 3/2009 | Tien et al. |
| 8,211,855 B2 * | 7/2012 | Chang et al. ............ 514/2.9 |
| 8,288,348 B2 * | 10/2012 | Chang et al. ............ 514/19.9 |
| 2001/0003589 A1 | 6/2001 | Neuer et al. |
| 2001/0036449 A1 | 11/2001 | Garst |
| 2002/0012680 A1 | 1/2002 | Patel et al. |
| 2002/0013272 A1 | 1/2002 | Cavanak et al. |
| 2002/0016290 A1 | 2/2002 | Floc'h et al. |
| 2002/0016292 A1 | 2/2002 | Richter et al. |
| 2002/0025927 A1 | 2/2002 | Olbrich et al. |
| 2002/0045601 A1 | 4/2002 | Kawashima et al. |
| 2002/0107183 A1 | 8/2002 | Petswzulat et al. |
| 2002/0119190 A1 | 8/2002 | Meinzer et al. |
| 2002/0165134 A1 | 11/2002 | Richter et al. |
| 2003/0060402 A1 | 3/2003 | Cavanak et al. |
| 2003/0133984 A1 | 7/2003 | Ambuhl et al. |
| 2003/0143250 A1 | 7/2003 | Hauer et al. |
| 2003/0147954 A1 | 8/2003 | Yang et al. |
| 2003/0166517 A1 | 9/2003 | Fricker et al. |
| 2003/0211983 A1 | 11/2003 | Petszulat et al. |
| 2003/0215496 A1 | 11/2003 | Patel et al. |
| 2004/0048789 A1 | 3/2004 | Patel |
| 2004/0101552 A1 | 5/2004 | Patel |
| 2004/0102366 A1 | 5/2004 | Patel |
| 2004/0161458 A1 | 8/2004 | Meinzer et al. |
| 2004/0167063 A1 | 8/2004 | Cavanak et al. |
| 2004/0191284 A1 * | 9/2004 | Yu et al. ............ 424/401 |
| 2004/0198645 A1 | 10/2004 | Ambuhl et al. |
| 2005/0048087 A1 | 3/2005 | Posanski |
| 2005/0059583 A1 | 3/2005 | Acheampong et al. |
| 2005/0118254 A1 | 6/2005 | Choi et al. |
| 2005/0129718 A1 | 6/2005 | Sherman |
| 2005/0147659 A1 | 7/2005 | Carli et al. |

OTHER PUBLICATIONS

Lasic, 1998, Pharmaceutical dosage forms; disperse system (Ed: Lieberman), p. 73.
Lecithin, Retrieved from: http://web.archive.org/web/20040711090238/http://en.wikipedia.org/wiki/Lecithin, 1 page, 2004 (retrieved on Nov. 14, 2009.
Restasis®(cyclosporine ophthalmic emulsion)0.05%, Sterile, Preserviatve-Free, 5 pages, Allergan, Irvine, California, 92612, USA, 2009, www.restasis.com.
Tibell, 1995, Pharmacology & Toxicology, 76, 115-121.
Office Action dated Jun. 13, 2006 for U.S. Appl. No. 11/181,509.
Office Action dated Oct. 23, 2006 for U.S. Appl. No. 11/181,509.
Office Action dated Mar. 29, 2007 for U.S. Appl. No. 11/181,509.
Office Action dated Jul. 13, 2007 for U.S. Appl. No. 11/181,509.
Office Action dated Mar. 20, 2006 for U.S. Appl. No. 11/255,821.
Office Action dated May 2, 2006 for U.S. Appl. No. 11/255,821.
Office Action dated Oct. 20, 2006 for U.S. Appl. No. 11/255,821.
Office Action dated Jan. 10, 2007 for U.S. Appl. No. 11/255,821.
Office Action dated Mar. 22, 2007 for U.S. Appl. No. 11/255,821.
Notice of Allowance dated Aug. 14, 2007 for U.S. Appl. No. 11/255,821.
Office Action dated May 31, 2006 for U.S. Appl. No. 11/181,178.
Office Action dated Aug. 9, 2006 for U.S. Appl. No. 11/181,178.
Office Action dated Dec. 1, 2006 for U.S. Appl. No. 11/181,178.
Notice of Allowance dated Aug. 22, 2007 for U.S. Appl. No. 11/181,178.
Office Action dated Aug. 10, 2007 for U.S. Appl. No. 11/161,218.
Office Action dated Nov. 15, 2005 for U.S. Appl. No. 11/181,409.
Office Action dated Jan. 10, 2006 for U.S. Appl. No. 11/181,409.
Office Action dated Feb. 22, 2006 for U.S. Appl. No. 11/181,409.
Office Action dated May 17, 2006 fo r U.S. Appl. No. 11/181,409.
Office Action dated Jan. 22, 2007 for U.S. Appl. No. 11/181,409.
Office Action dated Jun. 27, 2007 for U.S. Appl. No. 11/181,409.

* cited by examiner

CYCLOSPORIN COMPOSITIONS

CROSS REFERENCE TO RELATED APPLICATIONS

This application is a continuation of U.S. patent application Ser. No. 11/857,223, filed Sep. 18, 2007, now issued as U.S. Pat. No. 8,211,855, which is a divisional of U.S. patent application Ser. No. 11/255,821, filed on Oct. 19, 2005, now U.S. Pat. No. 7,288,520, which is a continuation-in-part of U.S. patent application Ser. No. 11/181,409, filed on Jul. 13, 2005, now abandoned, the entire disclosure of which is expressly incorporated herein by reference, and claims priority thereto.

U.S. patent application Ser. No. 11/255,821 is also a continuation-in-part of U.S. patent application Ser. No. 11/181,509, filed on Jul. 13, 2005, the entire disclosure of which is expressly incorporated herein by reference, and claims priority thereto.

U.S. patent application Ser. No. 11/255,821 is also a continuation-in-part of U.S. patent application Ser. No. 11/181,187, filed on Jul. 13, 2005, the entire disclosure of which is expressly incorporated herein by reference, and claims priority thereto.

U.S. patent application Ser. No. 11/255,821 is also a continuation-in-part of U.S. patent application Ser. No. 11/181,178, filed on Jul. 13, 2005, the entire disclosure of which is expressly incorporated herein by reference, and claims priority thereto.

U.S. patent application Ser. No. 11/255,821 is also a continuation-in-part of U.S. patent application Ser. No, 11/181,428, filed Jul. 13, 2005, the entire disclosure of which is expressly incorporated herein by reference, and claims priority thereto.

BACKGROUND

Description of the Relevant Art

Cyclosporins are a group of nonpolar cyclic oligopeptides with known immunosuppressant activity. In addition, as set forth in U.S. Pat. No. 4,839,342, cyclosporin (sometimes referred to in the literature as "cyclosporine") has been found as effective in treating immune medicated keratoconjunctivitis sicca (KCS or dry eye disease) in a patient suffering therefrom.

As hereinabove noted, cyclosporin comprises a group of cyclic oligopeptides and the major component thereof is cyclosporin A ($C_{82}H_{111}N_{11}O_{12}$) which has been identified along with several other minor metabolites, cyclosporin B through I. In addition, a number of synthetic analogs have been prepared.

In general, commercially available cyclosporins may contain a mixture of several individual cyclosporins which all share a cyclic peptide structure consisting of eleven amino acid residues with a total molecular weight of about 1,200, but with different substituents or configurations of some of the amino acids.

The activity of cyclosporins, as hereinabove noted, is as an immunosuppressant and in the enhancement or restoring of lacrimal gland tearing.

Unfortunately, the solubility of cyclosporin in water is extremely low and as elaborated in U.S. Pat. No. 5,051,402, it has been considered not merely difficult but practically impossible to prepare a pharmaceutical composition containing cyclosporin dissolved in an aqueous medium.

As reported, the solubility cyclosporin in water is between about 20 µg/ml to 30 µg/ml for cyclosporin A. Hence, heretofore prepared formulations incorporating cyclosporin have been prepared as oily solutions containing ethanol. However, these preparations limit the bioavailability to oral preparations and this is believed to be due to the separation of cyclosporin as a solid immediately after it comes into contact with water, such as in the mouth or eye of a patient.

Surface active agents such as polyoxyethylated castor oil have been utilized as solubilizers to inject preparations in order to prevent cyclosporin from separating. However, this also may give rise to safety problems (see U.S. Pat. No. 5,051,402).

U.S. Pat. No. 5,474,979 discloses a pharmaceutical composition in the form of a nonirritating emulsion which includes at least one cyclosporin in admixture with a higher fatty acid glyceride and polysorbate 80. More particularly, the cyclosporin may be cyclosporin A and the higher fatty acid glyceride may be castor oil.

U.S. Pat. No. 6,582,718 discloses an ophthalmic composition particularly in the form of eye-drops suitable for the treatment of diseases of the eye and surrounding areas. The composition contains a cyclosporin and a surfactant selected from polyoxyethylene fatty acid esters, polyoxyethylene alkylphenyl ethers and polyoxyethylene alkyl ethers, or mixtures thereof.

Copending U.S. Patent Application No. 60/503,137, filed Sep. 15, 2003, and U.S. patent application Ser. No. 10/865,638, filed Jun. 9, 2004 also disclose compositions of interest.

DESCRIPTION OF THE INVENTION

A composition is disclosed herein comprising from about 0.001% to about 0.4% cyclosporin A, castor oil, and a surfactant selected from the group consisting of alcohol ethoxylates, alcohols, alkyl glycosides, alkyl polyglycosides, alkylphenol ethoxylates, amine oxides, block polymers, carboxylated alcohol of alkylphenol ethoxylates, carboxylic acids/fatty acids, cellulose derivatives, ethoxylated alcohols, ethoxylated alkylphenols, ethoxylated aryl phenols, ethoxylated fatty acids, ethoxylated fatty acids, ethoxylated fatty esters and oils, fatty alcohols, fatty esters, glycol esters, lanolin-based derivatives, lecithin and lecithin derivatives, lignin and lignin derivatives, methyl esters, monoglycerides and derivatives, phosphalipids, polyacrylic acids, polyethylene glycols, polyethylene oxide-polypropylene oxide copolymers, polyethylene oxides, polymeric surfactants, polypropylene oxides, propoxylated alcohols, propoxylated alkyl phenols, propoxylated fatty acids, protein-based surfactants, sarcosine derivatives, silicone-based surfactants, sorbitan derivatives, stearates, sucrose and glucose esters and derivatives, and combinations thereof.

In certain embodiments, the composition is an ophthalmically acceptable emulsion.

In one embodiment, the concentration of cyclosporin A is from about 0.001% to about 0.1%.

While not intending to limit the scope of the invention in any way, one type of useful surfactant is a sorbitan ester. Examples include, but are not limited to, Polysorbate 20, Polysorbate 40, Polysorbate 60, and Polysorbate 80.

While not intending to limit the scope of the invention in any way, another type of useful surfactant is a stearate. Examples include, but are not limited to, glyceryl stearate, isopropyl stearate, polyoxyl stearate, propylene glycol stearate, and sucrose stearate.

While not intending to limit the scope of the invention in any way, another useful surfactant is polyethylene glycol.

While not intending to limit the scope of the invention in any way. Other useful surfactants comprise polyethylene oxide or polypropylene oxide. Examples, include, but are not limited to, polyethylene oxides, polypropylene oxides, polyethylene oxide, polypropylene oxide copolymers, alcohol ethoxylates, and alkylphenol ethoxylates.

While not intending to limit the scope of the invention in any way, another useful type of surfactant is an alkyl glycoside.

While not intending to limit the scope of the invention in any way, another useful type of surfactant is an alkyl polyglycoside.

While not intending to limit the scope of the invention in any way, another useful type of surfactant is a fatty alcohol.

While not intending to limit the scope of the invention in any way, another useful type of surfactant is a cellulose derivative, including, but not limited to, hydroxypropylmethyl cellulose (HPMC) and carboxymethyl cellulose (CMC).

While not intending to limit the scope of the invention in any way, another useful type of surfactant is a polyacrylic acid, including, but not limited to, a Carbomer.

While not intending to limit the scope of the invention in any way, another useful type of surfactant is a phosphalipid, including, but not limited to, phosphatidyl chloline and phosphatidyl serine.

Other useful surfactants include, but are not limited to:
Alcohols, including but not limited to,
Diglycerol®, which is available from Solvay Chemicals, Inc.;
Hetoxide GT-80®, which is available from Global-Seven, Inc.;
Lexemul BEO®, which is available from Index Chemical Co.;
Polyglycerol-3®, which is available from Solvay Chemicals, Inc.;
Redicote E Series®, which is available from Akzo Nobel Surface Chemistry LLC;
Simulsol OX 1005L®, which is available from Seppic Inc.;
Stanfax 567®, which is available from Para-Chem Standard Div.;
TA-1618®, which is available from Procter & Gamble;
Witconol H-31A®, which is available from Akzo Nobel Surface Chemistry LLC; and
Standard Div.;
Amine Oxide, including but not limited to,
AO-405®, which is available from Tomah Products®, Inc.;
AO-455®, which is available from Tomah Products®, Inc.;
AO 728 Special®, which is available from Tomah Products®, Inc.;
Barlox 12®, which is available from Lonza Inc.;
Barlox 14®, which is available from Lonza Inc.;
Burcoxide Lo®, which is available from Burlington Chemical Co.®, Inc.;
Caloxamine LO®, which is available from Pilot Chemical Co.;
Chemoxide CAW®, which is available from Chemron Corp.;
Chemoxide LM-30®, which is available from Chemron Corp.;
Chemoxide LO®, which is available from Chemron Corp.;
Chemoxide MO®, which is available from Chemron Corp.;
Colalux CAO-35®, which is available from Colonial Chemical Co.;
Colalux LO®, which is available from Colonial Chemical Co.;
DeMox CAPO®, which is available from DeForest Enterprises, Inc.;
DeMox CSG-30®, which is available from DeForest Enterprises, Inc.;
DeMox LAO®, which is available from DeForest Enterprises, Inc.;
Emcol L®, which is available from Crompton Corp.;
Empigen OB®, which is available from Huntsman LLC;
Empigen OS/A®, which is available from Huntsman LLC;
Foamox CDO®, which is available from Alzo International, Inc.;
Foamox DMM®, which is available from Alzo international, Inc.;
Foamox DMS®, which is available from Alzo International, Inc.;
Genaminox KC®, which is available from Clariant Corporation;
Genaminox LA®, which is available from Clariant Corporation;
Hartofoam SAO®, which is available from Hart Chemical Coma
Hartox DMCD®, which is available from Hart Chemical Corp.;
Lipowax DAT®, which is available from Lipo Chemicals, Inc.;
Lipowax PB Pastilles®, which is available from Lipo Chemicals, Inc.;
Mackamine C8®, which is available from The McIntyre Group;
Mackamine C10®, which is available from The McIntyre Group;
Mackamine C14®, which is available from The McIntyre Group;
Mackamine CAO®, which is available from The McIntyre Group;
Mackamine CO®, which is available from The McIntyre Group;
Mackamine LO®, which is available from The McIntyre Group;
Mackamine O2®, which is available from The McIntyre Group;
Mackamine SAO®, which is available from The McIntyre Group;
Mackamine SO®, which is available from The McIntyre Group;
Manx KCAO®, which is available from BASF Corp.;
Monalac MO®, which is available from Uniqema;
Norfox LDA®, which is available from Norman, Fox & Co.;
Rhodamox LO®, which is available from Rhodia, Inc.;
Schercamox C-AA®, which is available from Noveon®, Inc.;
Schercamox DMA®, which is available from Noveon®, Inc.;
Schercamox DML®, which is available from Noveon®, Inc.;
Schercamox DMM®, which is available from Noveon®, Inc.;
Schercamox DMS®, which is available from Noveon®, Inc.;
Tegotens DO®, which is available from Goldschmidt Chemical Corp.;
Tomah AO-14-2®, which is available from Tomah Products®, Inc.; and
Triaminox CDO®, which is available from Tri-Tex Co.®, Inc.;
Block Polymers, including but not limited to,
AL 2070®, which is available from Uniqema;
Antarox 17-R-2®, which is available from Rhodia, Inc.;
Antarox 25-R-2®, which is available from Rhodia, Inc.;
Antarox 31-R-1®, which is available from Rhodia, Inc.;
Antarox P-84®, which is available from Rhodia, Inc.;
Antarox P-104/H®, which is available from Rhodia, Inc.;

Amox BP-Series®, which is available from Crompton Corp.;
Chemonic 435®, which is available from Chemron Corp.;
Chemonic D-25®, which is available from Chemron Corp.;
Chemonic PL Series®, which is available from Chemron Corp.;
Ethox L-121®, which is available from Ethox Chemicals, LLC;
Ethox L-122®, which is available from Ethox Chemicals, LLC;
Genapol PF-10®, which is available from Clariant Corporation;
Genapol PF-20®, which is available from Clariant Corporation;
Genapol PF-40A®, which is available from Clariant Corporation;
Norfox 2-LF®, which is available from Norman, Fox & Co.;
Pluronic, which is available from BASF;
Simulsol NW 342®, which is available from Seppic Inc.;
T-Det BP-1®, which is available from Harcros Chemicals Inc.;
T-Det XD®, which is available from Harcros Chemicals Inc.;
T-Det XH®, which is available from Harms Chemicals Inc.;
Triton CF-32®, which is available from Dow Chemical Company;
Witconol 171®, which is available from Akzo Nobel Surface Chemistry LLC;
Witconol 324®, which is available from Akzo Nobel Surface Chemistry LLC;
Witconol 324D®, which is available from Akzo Nobel Surface Chemistry LLC; and
Witconol PD-2000®, which is available from Akzo Nobel Surface Chemistry LLC;
Carboxylated Alcohol or Alkylphenol Ethoxylates, including but not limited to,
Emcol CN-6®, which is available from Crompton Corp.;
Ethcarb®, which is available from Ethox Chemicals, LLC;
Gemtex WNT-Conc®, which is available from Finetex Inc.;
Incrodet TD7-C®, which is available from Croda Inc.;
Marlinat CM 105/80®, which is available from Sasol North America Inc.;
Marlowet 1072®, which is available from Sasol North America Inc.;
Marlowet 4530®, which is available from Sasol North America Inc.;
Marlowet 4530 LF®, which is available from Sasol North America Inc.;
Marlowet 4534®, which is available from Sasol North America Inc.;
Marlowet 4538®, which is available from Sasol North America Inc.;
Marlowet 4539®, which is available from Sasol North America Inc.;
Marlowet 4539 LF®, which is available from Sasol North America Inc.;
Marlowet 4541®, which is available from Sasol North America Inc.;
Miranate LEC-80®, which is available from Rhodia, Inc.;
Sandopan B®, which is available from Clariant Corporation;
Sandopan B Modified®, which is available from Clariant Corporation;
Sandopan LS-24 Gel®, which is available from Clariant Corporation; and
Surfine T-A®, which is available from Finetex Inc.;
Carboxylic Acids/Fatty Acids, including but not limited to,
Colaterge RAM®, which is available from Colonial Chemical Co.;
Colatrope INC®, which is available from Colonial Chemical Co.;
Crodacid B®, which is available from Croda Inc.;
DeTrope CA-100®, which is available from DeForest Enterprises, Inc.;
Latol MTO®, which is available from Georgia-Pacific Corp.;
Lumulse CC-33 K®, which is available from Lambent Technologies Corp.;
Mulls 2218®, which is available from Bemel Chemical Co.®, Inc.;
OL-600®, which is available from Procter & Gamble;
OL-800®, which is available from Procter & Gamble;
R-910®, which is available from Procter & Gamble;
S-210®, which is available from Procter & Gamble;
Sandopan DTC Acid®, which is available from Clariant Corporation;
Sandopan LS 24 N®, which is available from Clariant Corporation; and
Sandopan MA-18®, which is available from Clariant Corporation;
Ethoxylated Alcohols, including but not limited to,
Adsee 799®, which is available from Akzo Nobel Surface Chemistry LLC;
Adsee 799®, which is available from Crompton Corp.;
Alfonic 610-3.5 ®, which is available from Sasol North America Inc.;
Alfonic 810-2®, which is available from Sasol North America Inc.;
Alfonic 810-6®, which is available from Sasol North America Inc.;
Alfonic 1012-3®, which is available from Sasol North America Inc.;
Alfonic 1012-5®, which is available from Sasol North America Inc.;
Alfonic 1216CO-1.5®, which is available from Sasol North America Inc.;
Alfonic 1216CO-7®, which is available from Sasol North America Inc.;
Alfonic 1412-3®, which is available from Sasol North America Inc.;
Alfonic 1412-7®, which is available from Sasol North America Inc.;
Arlasolve 200®, which is available from Uniqema;
Arlasolve 200 Liquid®, which is available from Uniqema;
Armix 180-C®, which is available from Crompton Cop.;
Armix 183®, which is available from Crompton Corp.;
Armul 2404®, which is available from Akzo Nobel Surface Chemistry LLC;
Armul 2404®, which is available from Crompton Corp.;
Atlas EMJ-C®, which is available from Atlas Refinery Inc.;
Atlas G-2109®, which is available from Uniqema;
Atlas G-3886®, which is available from Uniqema;
Atlas G-3890®, which is available from Uniqema;
Bio Soft E-200®, which is available from Stepan Canada Inc.;
Bio Soft E-300®, which is available from Stepan Canada Inc.;
Bio Soft E-400®, which is available from Stepan Canada Inc.;
Bio Soft EN 600®, which is available from Stepan Canada Inc.;
Bio Soft TD-400®, which is available from Stepan Canada Inc.;
Bio Soft TD-630®, which is available from Stepan Canada Inc.;
Brij 30®, which is available from Uniqema;
Brij 52®, which is available from Uniqema;

Brij 56®, which is available from Uniqema;
Brij 58®, which is available from Uniqema;
Brij 72®, which is available from Uniqema;
Brij 76®, which is available from Uniqema;
Brij 78®, which is available from Uniqema;
Brij 93®, which is available from Uniqema;
Brij 97®, which is available from Uniqema;
Brij 98®, which is available from Uniqema;
Brij 700®, which is available from Uniqema;
Brij 700 S®, which is available from Uniqema;
Brij 721®, which is available from Uniqema;
Brij 721 S®, which is available from Uniqema;
Burcoterge CDG®, which is available from Burlington Chemical Co.®, Inc.;
Canasol AT 600®, which is available from Canamex Quimicos S.A de C.v;
Canasol AT 800®, which is available from Canamex Quimicos S.A de C.v;
Canasol AT 1200®, which is available from Canamex Quimicos S.A de C.v;
Canasol BJ 35®, which is available from Canamex Quimicos S.A de C.v;
Canasol BJ 36®, which is available from Canamex Quimicos S.A de C.v;
Canasol BJ 52®, which is available from Canamex Quimicos S.A de C.v;
Canasol BJ 58®, which is available from Canamex Quimicos SA de C.v;
Canasol BJ 72®, which is available from Canamex Quimicos S.A de C.v;
Canasol BJ 78®, which is available from Canamex Quimicos S.A de C.v;
Canasol BJ 98®, which is available from Canamex Quimicos S.A de C.v;
Canasol BJ 307®, which is available from Canamex Quimicos S.A de C.v;
Cerfak 1400®, which is available from Houghton International Inc.;
Cetomacrogol 1000 BP®, which is available from Croda Inc.;
Chemonic C-2®, which is available from Chemron Corp.;
Chemonic C-10®, which is available from Chemron Corp.;
Chemonic C-20®, which is available from Chemron Corp.;
Chemonic CT-12®, which is available from Chemron Corp.;
Chemonic CT-20®, which is available from Chemron Corp.;
Chemonic CT-30®, which is available from Chemron Corp.;
Chemonic CT-55®, which is available from Chemron Corp.;
Chemonic G-7®, which is available from Chemron Corp.;
Chemonic G-26®, which is available from Chemron Corp.;
Chemonic L-4®, which is available from Chemron Corp.;
Chemonic L-7®, which is available from Chemron Corp.;
Chemonic L-12®, which is available from Chemron Corp.;
Chemonic L-23®, which is available from Chemron Corp.;
Chemonic O-2®, which is available from Chemron Corp.;
Chemonic O-5®, which is available from Chemron Corp.;
Chemonic O-10®, which is available from Chemron Corp.;
Chemonic O-20®, which is available from Chemron Corp.;
Chemonic S-2®, which is available from Chemron Corp.;
Chemonic S-10®, which is available from Chemron Corp.;
Chemonic S-20®, which is available from Chemron Corp.;
Colamulse FE®, which is available from Colonial Chemical Co.;
Cremophor A 20®, which is available from BASF Corp.;
Cremophor SA 2®, which is available from BASF Corp.;
Dehydrol 100®, which is available from Cognis Canada Corp.;
Dehydrol O-4®, which is available from Cognis Canada Corp.;
DeSonic C-18®, which is available from DeForest Enterprises, Inc.;
DeSonic 6T®, which is available from Crompton Corp.;
DeSonic 9D®, which is available from Crompton Corp.;
DeSonic 9T®, which is available from Crompton Corp.;
DeSonic 12D®, which is available from Crompton Corp.;
DeSonic 12T®, which is available from Crompton Corp.;
DeSonic 15T®, which is available from Crompton Corp.;
DeSonic TDA-9®, which is available from Crompton Corp.;
DeThox GLG-7®, which is available from DeForest Enterprises, Inc.;
DeThox GLG-26®, which is available from DeForest Enterprises, Inc.;
DeThox LA-4®, which is available from DeForest Enterprises, Inc.;
DeThox LA-23®, which is available from DeForest. Enterprises, Inc.;
DeThox SA-80®, which is available from DeForest Enterprises, Inc.;
Disponil O5®, which is available from Cognis Corporation;
Eccoterge EO-41B®, which is available from Eastern Color & Chemical Co.;
Empilan KA2.5/90®, which is available from Huntsman LLC;
Empilan KA5/90®, which is available from Huntsman LLC;
Empilan KM-20®, which is available from Huntsman LLC;
Empilan KM-50®, which is available from Huntsman LLC;
Empilan L-23®, which is available from Huntsman LLC;
Ethylan 25-3®, which is available from Akzo Nobel Surface Chemistry LLC;
Ethylan 1204®, which is available from Akzo Nobel Surface Chemistry LLC;
Ethylan DA-4®, which is available from Akzo Nobel Surface Chemistry LLC;
Ethylan LA-230®, which is available from Akzo Nobel Surface Chemistry LLC;
Ethylan SN®, which is available from Akzo Nobel Surface Chemistry LLC;
Ethylan TD-60®, which is available from Akzo Nobel Surface Chemistry LLC;
Ethylan TD-100®, which is available from Akzo Nobel Surface Chemistry LLC;
Ethylan TD-1407®, which is available from Akzo Nobel Surface Chemistry LLC;
Eumulgin B1®, which is available from Cognis Canada Corp.;
Eumulgin B2®, which is available from Cognis Canada Corp.;
Eumulgin B3®, which is available from Cognis Canada Corp.;
Eumulgin O-10®, which is available from Cognis Canada Corp.;
Flo Mo 80/20®, which is available from Crompton Corp.;
Flo Mo Low Foam®, which is available from Crompton Corp.;
Forlan C-24®, which is available from RITA Corp.;
Genapol 1454®, which is available from Clariant Corporation;
Genapol BA-020®, which is available from Clariant Corporation;
Genapol BA-040®, which is available from Clariant Corporation;
Genapol C-100®, which is available from Clariant Corporation;
Genapol DA 06®, which is available from Clariant Corporation;
Genapol 020®, which is available from Clariant Corporation;

Genapol HS 200®, which is available from Clariant Corporation;
Genapol ID-040®, which is available from Clariant Corporation;
Genapol ID-060®, which is available from Clariant Corporation;
Genapol ID-090®, which is available from Clariant Corporation;
Genapol LA 010®, which is available from Clariant Corporation;
Genapol LA 020®, which is available from Clariant Corporation;
Genapol LA 030®, which is available from Clariant Corporation;
Genapol LA 040®, which is available from Clariant Corporation;
Genapol LA 050®, which is available from Clariant Corporation;
Genapol LA 060®, which is available from Clariant Corporation;
Genapol LA 070®, which is available from Clariant Corporation;
Genapol LA 070S®, which is available from Clariant Corporation;
Genapol LA 230®, which is available from Clariant Corporation;
Genapol O 020®, which is available from Clariant Corporation;
Genapol O 050®, which is available from Clariant Corporation;
Genapol O 100®, which is available from Clariant Corporation;
Genapol O 200®, which is available from Clariant Corporation;
Genapol SA 030®, which is available from Clariant Corporation;
Genapol SA 120®, which is available from Clariant Corporation;
Genapol T-020®, which is available from Clariant Corporation;
Genapol UD-030®, which is available from Clariant Corporation;
Genapol UD-050®, which is available from Clariant Corporation;
Genapol UD-070®, which is available from Clariant Corporation;
Genapol UD-079®, which is available from Clariant Corporation;
Genapol UD-080®, which is available from Clariant Corporation;
Genapol UD-110®, which is available from Clariant Corporation;
Genapol X 030®, which is available from Clariant Corporation;
Genapol X 050®, which is available from Clariant Corporation;
Genapol X 060®, which is available from Clariant Corporation;
Genapol X 070®, which is available from Clariant Corporation;
Genapol X 080®, which is available from Clariant Corporation;
Genapol X 100®, which is available from Clariant Corporation;
Genapol X159®, which is available from Clariant Corporation;
Generol 122 E5®, which is available from Cognis Canada Corp.;
Generol 122 E25®, which is available from Cognis Canada Corp.;
Hostacerin T-3®, which is available from Clariant Corporation;
Iconol LF 110®, which is available from BASF Corp.;
Incropol CS-20®, which is available from Croda Inc.;
Lexemul CS-20®, which is available from Index Chemical Co.;
Liponic ES-1®, which is available from Lipo Chemicals, Inc.;
Lipowax D®, which is available from Lipo Chemicals, Inc.;
Lipowax G®, which is available from Lipo Chemicals, Inc.;
Lipowax NI®, which is available from Lipo Chemicals, Inc.;
Lipowax P®, which is available from Lipo Chemicals, Inc.;
Lipowax P-31®, which is available from Lipo Chemicals, Inc.;
Lipowax PR®, which is available from Lipo Chemicals, Inc.;
Lumulse CS-20®, which is available from Lambent Technologies Corp.;
Macol CSA-20®, which is available from BASF Corp.;
Marlox B 24/50®, which is available from Sasol North America Inc.;
Mazawet 77®, which is available from BASF Corp.;
Norfox 1713®, which is available from Norman, Fox & Co.;
Norfox 2579®, which is available from Norman, Fox & Co.;
Norfox Lo Foam®, which is available from Norman, Fox & Co.;
Promulgen D®, which is available from Amerchol Corp.;
Promulgen G®, which is available from Amerchol Corp.;
Renex 30®, which is available from Uniqema;
Reflex 36®, which is available from Uniqema;
Rhodasurf A 24®, which is available from Rhoda, Inc.;
Rhodasurf AAE-10®, which is available from Rhodia, Inc.;
Rhodasurf BEH-25®, which is available from Rhodia, Inc.;
Rhodasurf BEH-40®, which is available from Rhodia, Inc.;
Rhodasurf DA 530®, which is available from Rhodia, Inc.;
Rhodasurf DA 630®, which is available from Rhodia, Inc.;
Rhodasurf DA 639®, which is available from Rhodia, Inc.;
Rhodasurf LAN-23®, which is available from Rhodia, Inc.;
Rhodasurf ON-870®, which is available from Rhodia, Inc.;
Rhodasurf ON-877®, which is available from Rhodia, Inc.;
Rhodasurf TB-970 FLK®, which is available from Rhodia, Inc.;
Ritacet-20®, which is available from RITA Corp.;
Ritachol 1000 ®, which is available from RITA Corp.;
Ritachol 2000®, which is available from RITA Corp.;
Ritachol 5000®, which is available from RITA Corp.;
Ritox 35®, which is available from RITA Corp.;
Surfonic DA-4®, which is available from Huntsman LLC;
Surfonic DA-6®, which is available from Huntsman LLC;
Surfonic L46-7®, which is available from Huntsman LLC;
Surfonic POA®, which is available from Huntsman LLC;
Synthrapol KB®, which is available from Uniqema;
Teginacid®, which is available from Goldschmidt Chemical Corp.;
Teginacid C®, which is available from Goldschmidt Chemical Corp.;
Tegotens EC 11®, which is available from Goldschmidt Chemical Corp.;
Tinegal NA®, which is available from Ciba Specialty Chemicals Corp.;
Tomadol 400®, which is available from Tomah Products®, Inc.;
Tomadol 600®, which is available from Tomah Products®, Inc.;

Tomadol 900®, which is available from Tomah Products®, Inc.;
Uniperol O®, which is available from BASF Corp.;
Witconol SN Series®, which is available from Crompton Corp.;
Ethoxylated Alkylphenois, including but not limited to,
Antarox LF-222®, which is available from Rhodia, Inc.;
Atlox 775®, which is available from Uniqema;
Caloxylate N-9®, which is available from Pilot Chemical Co.;
Canasol NF-1000®, which is available from Canamex Quimicos S.A de C.v;
Canasol NF-3000®, which is available from Canamex Quimicos S.A de C.v;
Canasol NP-3070®, which is available from Canamex Quimicos S.A de C.v;
Canasol OF 1670®, which is available from Canamex Quimicos S.A de C.v;
Canasol OF 2570®, which is available from Canamex Quimicos S.A de C.v;
Canasol OF 4070®, which is available from Canamex Quimicos S.A de C.v;
Chemax DNP-8®, which is available from Chemax Performance Solutions;
Chemax DNP-18®, which is available from Chemax Performance Solutions;
Chemax DNP-150/50®, which is available from Chemax Performance Solutions;
DeSonic 1.5N®, which is available from Crompton Corp.;
DeSonic 4N®, which is available from Crompton Corp.;
DeSonic 5N®, which is available from Crompton Corp.;
DeSonic 6D®, which is available from Crompton Corp.;
DeSonic 6N®, which is available from Crompton Corp.;
DeSonic 7N®, which is available from Crompton Corp.;
DeSonic 9N®; which is available from Crompton Corp.;
DeSonic 10D®, which is available from Crompton Corp.;
DeSonic 11N®, which is available from Crompton Corp.;
DeSonic 12N®, which is available from Crompton Corp.;
DeSonic 15N®, which is available from Crompton Corp.;
DeSonic 20N®, which is available from Crompton Corp.;
Eccoscour RC®, which is available from Eastern Color & Chemical Co.;
Eccoterge EO-100®, which is available from Eastern Color & Chemical Co.;
Emulsifier 632/90%®, which is available from Ethox Chemicals, LLC;
Geronol AG-821®, which is available from Rhodia, Inc.;
Gradonic N-95®, which is available from Graden Chemical Co. Inc.;
Hetoxide NP-4®, which is available from Global-Seven, Inc.;
Hetoxide NP-30®, which is available from Global-Seven, Inc.;
Hostapal N-100®, which is available from Clariant Corporation;
Hostapal N-110®, which is available from Clariant Corporation;
Igepal CTA-639W®, which is available from Rhodia, Inc.;
Igepal DAP-9®, which is available from Rhodia, Inc.;
Igepal OD-410®, which is available from Rhodia, Inc.;
Igepal SS-837®, which is available from Rhodia, Inc.;
Lipocol NP-9 USP®, which is available from Lipo Chemicals, Inc.;
Macol DNP-10®, which is available from BASF Corp.;
Marlophen NP 5®, which is available from Sasol North America Inc.;
Marlophen P 1®, which is available from Sasol North America Inc.;
Surfonic NB®, which is available from Huntsman LLC;
Surfonic OPB-307®, which is available from Huntsman LLC;
Surfonic OPB-407®, which is available from Huntsman LLC;
Syn Fac 334®, which is available from Milliken Chemical;
Syn Fac 8216®, which is available from Milliken Chemical;
Triton N-57®, which is available from Dow Chemical Company;
Trycol 6956®, which is available from Cognis Corporation;
Trycol 6961®, which is available from Cognis Corporation;
Trycol 6964®, which is available from Cognis Corporation;
Trycol 6969®, which is available from Cognis Corporation;
Trycol 6974®, which is available from Cognis Corporation;
Witbreak DRB-127®, which is available from Akzo Nobel Surface Chemistry LLC;
Witbreak DRB-127®, which is available from Crompton Corp.; and
Witconol NP Series®, which is available from Akzo Nobel Surface Chemistry LLC;
Ethoxylated Aryl Phenols, including but not limited to,
Soprophor BSU®, which is available from Rhodia, Inc.;
Soprophor CY/8®, which is available from Rhodia, Inc.;
Soprophor S/25®, which is available from Rhodia, Inc.;
Witconol NIO®, which is available from Akzo Nobel Surface Chemistry LLC;
Witconol NIW®, which is available from Akzo Nobel Surface Chemistry LLC; and
Witconol S-100®, which is available from Akzo Nobel Surface Chemistry LLC;
Ethoxylated Fatty Acids, including but not limited to,
Aldo PGHMS®, which is available from Lonza Inc.;
Alkamuis 10-15/HR®, which is available from Rhodia, Inc.;
Armotan AL-69-66®, which is available from Akzo Nobel Surface Chemistry LLC;
Cerasynt 840®, which is available from International Specialty Products/IS;
Cerasynt 945®, which is available from International Specialty Products/IS;
Crystal Inhibitor No. 5®, which is available from Harcros Chemicals Inc.;
DeThox Acid L-9®, which is available from DeForest Enterprises, Inc.;
DeThox Acid S-8®, which is available from DeForest Enterprises, Inc.;
Ethofat 242/25®, which is available from Akzo Nobel Surface Chemistry LLC;
Hydropalat 65®, which is available from Cognis Corporation;
Lipo EGMS®, which is available from Lipo Chemicals, Inc.;
Lipopeg 2 DL®, which is available from Lipo Chemicals, Inc.;
Lipopeg 4 DL®, which is available from Lipo Chemicals, Inc.;
Lipopeg 4-L®, which is available from Lipo Chemicals, Inc.;
Lipopeg 39-S®, which is available from Lipo Chemicals, Inc.;
Lipopeg 4-S®, which is available from Lipo Chemicals, Inc.;
Lipopeg 10-S®, which is available from Lipo Chemicals, Inc.;
Lipopeg 100-S®, which is available from Lipo Chemicals, Inc.;
Lipopeg 6000 DS®, which is available from Lipo Chemicals; Inc.;
Lumulse 40-L®, which is available from Lambent Technologies Corp.;

Lumulse 40-S®, which is available from Lambent Technologies Corp.;
Lumulse 42-L®, which is available from Lambent Technologies Corp.;
Lumulse 42-S®, which is available from Lambent Technologies Corp.;
Lumulse 100-S®, which is available from Lambent Technologies Corp.;
Lumulse 602-S®, which is available from Lambent Technologies Corp.;
Magrabar PGE-20-O®, which is available from Magrabar Chemical Corp.;
Magrabar PGE-20L®, which is available from Magrabar Chemical Corp.;
Magrabar PGE-20T®, which is available from Magrabar Chemical Corp.;
Magrabar PGE-22-O®, which is available from Magrabar Chemical Corp.;
Magrabar PGE-22L®, which is available from Magrabar Chemical Corp.;
Magrabar PGE-22T®, which is available from Magrabar Chemical Corp.;
Magrabar PGE-40-O®, which is available from Magrabar Chemical Corp.;
Magrabar PGE-40L®, which is available from Magrabar Chemical Corp.;
Magrabar PGE-40T®, which is available from Magrabar Chemical Corp.;
Magrabar PGE-42-O®, which is available from Magrabar Chemical Corp.;
Magrabar PGE-42L®, which is available from Magrabar Chemical Corp.;
Magrabar PGE-42T®, which is available from Magrabar Chemical Corp.;
Magrabar PGE-60-O®, which is available from Magrabar Chemical Corp.;
Magrabar PGE-60L®, which is available from Magrabar Chemical Corp.;
Magrabar PGE-60T®, which is available from Magrabar Chemical Corp.;
Magrabar PGE-62-O®, which is available from Magrabar Chemical Corp.;
Magrabar PGE-62L®, which is available from Magrabar Chemical Corp.;
Magrabar PGE-62T®, which is available from Magrabar Chemical Corp.;
Mapeg S-40K®, which is available from BASF Corp.;
Marlowet OTS®, which is available from Sasol North America Inc.;
Naturechem PGR®, which is available from CasChem®; Inc.;
PG No. 4®, which is available from Hart Chemical Corp.;
Renex 20®, which is available from Uniqema;
Ritox 52®, which is available from RITA Corp.;
Ritox 53®, which is available from RITA Corp.;
Ritox 59®, which is available from RITA Corp.;
Surtax 8916/A®, which is available from Houghton International Inc.;
Tego Acid S 40 P®, which is available from Goldschmidt Chemical Cop.;
Tego Acid S 100 P®, which is available from Goldschmidt Chemical Corp.;
Tween 20®, which is available from Uniqema; and
Volpo 131®, which is available from Croda Inc.;
Ethoxylated Fatty Esters or Oils (Animal & Veg.), including but limited to
Acconon 6-C10®, which is available horn Abitec Corporation;
Acconon CC-6®, which is available from Abitec Corporation;
Acconon CO-7®, which is available from Abitec Corporation;
Aldosperse 40/60 FG®, which is available from Lonza Inc.;
Aldosperse ML-23®, which is available from Lonza Inc.;
Aldosperse MS-20 FG®, which is available from Lonza Inc.;
Alkamuls EL-620®, which is available from Rhodia, Inc.;
Alkamuls EL-719®, which is available from Rhodia, Inc.;
Alkamuls EL-985®, which is available from Rhodia, Inc.;
Arlatone G®, which is available from Uniqema;
Arlatone T®, which is available from Uniqema;
Atlas G-104A®, which is available from Uniqema;
Atlas G-1086®, which is available from Uniqema;
Atlas G-1087®, which is available from Uniqema;
Atlas G-1089®, which is available from Uniqema;
Atlas G-1096®, which is available from Uniqema;
Atlas G-1292®, which is available from Uniqema;
Atlas G-1293®, which is available from Uniqema;
Atlas G-1300®, which is available from Uniqema;
Atlas G-7076®, which is available from Uniqema;
Capmul EMG®, which is available from Abitec Corporation;
Chemonic CO-40®, which is available from Chemron Corp.;
Chemonic LI-3®, which is available from Chemron Corp.;
Chemonic LI-7®, which is available from Chemron Corp.;
Cirrasol GM®, which is available from Uniqema;
Cremophor CO 40®, which is available from BASF Corp.;
Cremophor CO 410®, which is available from BASF Corp.;
Cremophor EL®, which is available from BASF Corp.;
Cremophor GC7®, which is available from BASF Corp.;
Cremophor RH-40®, which is available from BASF Corp.;
Crovol A-40®, which is available from Croda Inc.;
Crovol A-70®, which is available from Croda Inc.;
Crovol M-70®, which is available from Croda Inc.;
Crovol PK-70®, which is available from Croda Inc.;
Cutina E-24®, which is available from Cognis Canada Corp.;
Dacospin 12-R®, which is available from Cognis Corporation;
Dehymuls HRE-7®, which is available from Cognis Corporation;
DeSonic 30C®, which is available from Crompton Corp.;
DeSonic 36C®, which is available from Crompton Corp.;
DeSonic 40C®, which is available from Crompton Corp.;
Durfax 60®, which is available from Loders Croklaan U.S.A.;
Durfax 65®, which is available from Loders Croklaan U.S.A.;
Durfax 80®, which is available from Loders Croklaan U.S.A.;
Durfax EOM®, which is available from Loders Croklaan U.S.A.;
Eccoterge NF-2®, which is available from Eastern Color & Chemical Co.;
Emulpon CO-360®, which is available from Akzo Nobel Surface Chemistry LLC;
Emulpon CO-550®, which is available from Akzo Nobel Surface Chemistry LLC;
Emulsogen EL®, which is available from Clariant Corporation;
Emulsogen HCO 040®, which is available from Clariant Corporation;
Emulsogen HCO 060®, which is available from Clariant Corporation;
Emulsynt 1055®, which is available from International Specialty Products/IS;

Ethox 3095®, which is available from Ethox Chemicals, LLC;
Eumulgin RO-40®, which is available from Cognis Canada Corp.;
Genapol G-260®, which is available from Clariant Corporation;
Glycosperse L-20®, which is available from Lonza Inc.;
Glycosperse O-5®, which is available from Lonza Inc.;
Glycosperse O-20®, which is available from Lonza Inc.;
Glycosperse O-20 FG®, which is available from Lonza Inc.;
Glycosperse S-20®, which is available from Lonza Inc.;
Glycosperse S-20 FG®, which is available from Lonza Inc.;
Glycosperse TS-20®, which is available from Lonza Inc.;
Glycosperse TS-20 FG®, which is available from Lonza Inc.;
Hetan SL®, which is available from Global-Seven, Inc.;
Hetan SO®, which is available from Global-Seven, Inc.;
Hetan SS®, which is available from Global-Seven, Inc.;
Hetoxide C-2®, which is available from Global-Seven, Inc.;
Hetoxide C-9®, which is available from Global-Seven, Inc.;
Hetoxide C-15®, which is available from Global-Seven, Inc.;
Hetoxide C-25®, which is available from Global-Seven, Inc.;
Hetoxide C-40®, which is available from Global-Seven, Inc.;
Hetoxide C-200®, which is available from Global-Seven, Inc.;
Hetoxide C-200-50%®, which is available from Global-Seven, Inc.;
Hetoxide GC-30®, which is available from Global-Seven, Inc.;
Hetoxide HC-60®, which is available from Global-Seven, Inc.;
Ice No. 2®, which is available from Loders Croklaan
Incrocas 30/40®, which is available from Croda Inc.;
Lexol EC®, which is available from index Chemical Co.;
Lexol EO®, which is available from Index Chemical Co.;
Lipocol HCO-40®, which is available from Lipo Chemicals, Inc.;
Lipocol HCO-60®, which is available from Lipo Chemicals, Inc.;
Lipocol O-3 Special®, which is available from Lipo Chemicals, Inc.;
Lipopeg 2-L®, which is available from Lipo Chemicals, Inc.;
Lipopeg 4-DO®, which is available from Lipo Chemicals, Inc.;
Lipopeg 4-DS®, which is available from Lipo Chemicals, Inc.;
Lipovol GTB®, which is available from Lipo Chemicals, Inc.;
Lonzest SML-20®, which is available from Lonza Inc.;
Lonzest SMO-20®, which is available from Lonza Inc.;
Lonzest SMS-20®, which is available from Lonza Inc.;
Lonzest STO-20®, which is available from Lonza Inc.;
Lonzest STS-2P, which is available from Lonza Inc.;
Lumulse GR-40®, which is available from Lambent Technologies Corp.;
Lumulse GRH-40®, which is available from Lambent Technologies Corp.;
Lumulse POE (7) GML®, which is available from Lambent Technologies Corp.;
Lumulse POE (12) Glyc®, which is available from Lambent Technologies Corp.;
Lumulse POE (40) MS KP®, which is available from Lambent Technologies Corp.;
Marlowet 4750®, which is available from Sasol North America Inc.;
Marlowet LVS®, which is available from Sasol North America Inc.;
Marlowet R 11®, which is available from Sasol North America Inc.;
Marlowet R 40®, which is available from Sasol North America Inc.;
Mazol 80 MGK®, which is available from BASF Corp.;
Nonionic Emulsifier T-9®, which is available from Werner G. Smith Inc.;
Oronal LCG®, which is available from Seppic Inc.;
Polyderm PPI-CO-200®, which is available from Alzo International, Inc.;
Polyderm PPI-CO-40®, which is available from Alzo International, Inc.;
Rewoderm LI 520-70®, which is available from Goldschmidt Chemical Corp.;
Ritapeg 150 DS®, which is available from RITA Corp.;
Softigen 767®, which is available from Sasol North America Inc.;
Surfactol 318®, which is available from CasChem®, Inc.;
Surfactol 365®, which is available from CasChem®, Inc.;
Syn Lube 107®, which is available from Milliken Chemical;
Syn Lube 728®, which is available from Milliken Chemical;
Syn Lube 1632H®, which is available from Milliken Chemical;
Syn Lube 6277-A®; which is available from Milliken Chemical;
T-Det C-20®, which is available from Harcros Chemicals Inc.;
T-Det C-40®, which is available from Harms Chemicals Inc.;
Tally 100 Plus®, which is available from Loders Croklaan U.S.A.; and
Uniperol EL®, which is available from BASF Corp.;
Fatty Esters, including but not limited to,
Actralube-Syn 147®, which is available from Georgia-Pacific Corp.;
Atlas G-1556®, which is available from Uniqema;
Atlas G-1564®, which is available from Uniqema;
Atlasol Base Oil S®, which is available from Atlas Refinery Inc.;
Base ML®, which is available from Keil Chemical;
Base MT®, which is available from Keil Chemical;
Cerasynt 303®, which is available from International Specialty Products/IS;
Dermol 1012®, which is available from Alzo International, Inc.;
Kemester 4000®, which is available from Crompton Corp.;
Lactipol S®, which is available from Canamex Quimicos S.A de C.v;
Magrabar PGO®, which is available from Magrabar Chemical Corp.;
Mayco Base BFO®, which is available from Dover Chemical Corp.;
Methyl Linoleate®, which is available from Hart Chemical Corp.;
Pationic 122A®, which is available from RITA Corp.;
Pationic 138C®, which is available from RITA Corp.;
Pationic CSL®, which is available from RITA Corp.;
Pationic ISL®, which is available from RITA Corp.;
Pationic SBL®, which is available from RITA Corp.;
Pationic SSL®, which is available from RITA Corp.;
Ritasol®, which is available from RITA Corp.;
Tego Alkanol CS 20®, which is available from Goldschmidt Chemical Corp.;
Tego Alkanol L23 P®, which is available from Goldschmidt Chemical Corp.;
Tego Alkanol S2®, which is available from Goldschmidt Chemical Corp.;

Tego Alkanol S20 P®, which is available from Goldschmidt Chemical Corp.; and

Triemulsifier 600 MS®, which is available from Tri-Tex Co.®, Inc.;

Glycerol Esters, including but not limited to,

Agro #9 Wint SBO®, which is available from Lambent Technologies Corp.;

Ahcovel Base 700®, which is available from Uniqema;

Aldo HMS FG®, which is available from Lonza Inc.;

Aldo MLD®, which is available from Lonza Inc.;

Aldo MLD FG®, which is available from Lonza Inc.;

Aldo MO FG®, which is available from Lonza Inc.;

Aldo MS®, which is available from Lonza Inc.;

Aldo MS FG®, which is available from Lonza Inc.;

Aldo MS LG FG®, which is available from Lonza Inc.;

Aldo MSD®, which is available from Lonza Inc.;

Aldo MSD FG®, which is available from Lonza Inc.;

Aldosperse O-20 FG®, which is available from Lonza Inc;

Aldosperse TS-20 FG®, which is available from Lonza Inc.;

Aldosperse TS-40 FG®, which is available from Lonza Inc.;

Arlacel 165®, which is available from Uniqema;

Arlacel 186®, which is available from Uniqema;

Capmul GMO®, which is available from Abitec Corporation;

Capmul GMS®, which is available from Abitec Corporation;

Caprol 3GO®, which is available from Abitec Corporation;

Caprol 3GVS®, which is available from Abitec Corporation;

Caprol 6G2S®, which is available from Abitec Corporation;

Caprol 10G40®, which is available from Abitec Corporation;

Caprol 10G100®, which is available from Abitec Corporation;

Caprol ET®, which is available from Abitec Corporation;

Caprol PGE860®, which is available from Abitec Corporation;

Cerasynt 945®, which is available from International Specialty Products/IS;

Cerasynt GMS®, which is available from International Specialty Products/IS;

Cerasynt Q®, which is available from International Specialty Products/IS;

Cerasynt SD®, which is available from International Specialty Products/IS;

Cerasynt WM®, which is available from International Specialty Products/IS;

Chemsperse 14®, which is available from Chemron Corp.;

Cremophor GO-32®, which is available from BASF Corp.;

Cremophor GS11®, which is available from BASF Corp.;

Cremophor GS-32®, which is available from BASF Corp.;

Cutina KD-16®, which is available from Cognis Canada Corp.;

Dehymuls PGPH®, which is available from Cognis Corporation;

Dermol DGDIS®, which is available from Alzo international, Inc.;

Dermal DGMIS®, which is available from Alzo International, Inc.;

Dermol G-78®, which is available from Alzo International; Inc.;

Dermol G-7DI®, which is available from Alzo International, Inc.;

Dermol NGDI®, which is available from Alzo International, Inc.;

Dermolan GLH®, which is available from Alzo International, Inc.;

Drewmulse GMO®, which is available from Stepan Company;

Drewpol 3-5-M®, which is available from Stepan Company;

Durlac 100 W®, which is available from Loders Croklaan U.S.A.;

Dur-Lo®, which is available from Loders Croklaan

Dynasan 118®, which is available from Sasol North America Inc.;

EC-25®, which is available from Loders Croklaan U.S.A.;

EM 40®, which is available from Keil Chemical;

Emerest 2400®, which is available from Cognis Corporation;

Emerest 2452®, which is available from Cognis Corporation;

Empilan G-26®, which is available from Huntsman LLC;

Genapol TSM®, which is available from Clariant Corporation;

Hostacerin DGI®, which is available from Clariant Corporation;

Hostacerin DGL®, which is available from Clariant Corporation;

Hostacerin DGMS®, which is available from Clariant Corporation;

Hostacerin DGSB®, which is available from Clariant Corporation;

Ice No. 2®, which is available from Loders Croklaan U.S.A.;

Imwitor 742®, which is available from Sasol North America Inc.;

Imwitor 780 K®, which is available from Sasol North America Inc.;

Imwitor 960 Flakes®, which is available from Sasol North America Inc.;

Isolan GI 34®, which is available from Goldschmidt Chemical Corp.;

Isolan GO 33®, which is available from Goldschmidt Chemical Corp.;

Kemester 1000®, which is available from Crompton Corp.;

Kemester 2000®, which is available from Crompton;

Kemester 2000®, which is available from Crompton Corp.;

Kemester 6000SE®, which is available from Crompton Corp.;

Lamecreme DGE 18®, which is available from Cognis Corporation;

Lexemul 515®, which is available from Molex Chemical Co.;

Lexemul 561®, which is available from Index Chemical Co.;

Lexemul AR®, which is available from Inolex Chemical Co.;

Lexemul AS®; which is available from Inolex Chemical Co.;

Lexemul GDL®, which is available from Inolex Chemical Co.;

Lexemul 7, which is available from Inolex Chemical Co.;

Lipomulse 165®, which is available from Lipo Chemicals, Inc.;

Lumulse GML K®, which is available from Lambent Technologies Corp.;

Lumulse GMO K®, which is available from Lambent Technologies Corp.;

Lumulse GAR K®, which is available from Lambent Technologies Corp.;

Lumulse GMT K®, which is available from Lambent Technologies Corp.;

Magrabar GMC®, which is available from Magrabar Chemical Corp.;

Magrabar GMO-CK®, which is available from Magrabar Chemical Corp.;

Magrabar MDG-5050®, which is available from Magrabar Chemical Corp.;

Magrabar PGO-315®, which is available from Magrabar Chemical Cop.;

Magrabar PGO-1010®, which is available from Magrabar Chemical Corp.;

Mazol 300K®, which is available from BASF Cop.;

Mazol GMO-K®, which is available from BASF Corp.;

Mazol GMS-K®, which is available from BASF Corp.;
Mazol PG031-K®, which is available from BASF Corp.;
Miglyol 812®, which is available from Sasol North America Inc.;
Norfox 165C®, which is available from Norman, Fox & Co.;
Schercemol GMIS®, which is available from Noveon®, Inc.;
Tegin®, which is available from Goldschmidt Chemical Cop.;
Tegin 4100 Pellets®, which is available from Goldschmidt Chemical Corp.;
Tegin M Pellets®, which is available from Goldschmidt Chemical Corp.;
Tegin OV®, which is available from Goldschmidt Chemical Corp.;
Teginacid H®, which is available from Goldschmidt Chemical Corp.;
Tego Cosmo P813®, which is available from Goldschmidt Chemical Corp.;
Wickenol 535®, which is available from Alzo International, Inc.;
Witconol 14®, which is available from Akzo Nobel Surface Chemistry LLC;
Witconol 14®, which is available from Crompton Corp.;
Witconol 14F®, which is available from Crompton Corp.;
Witconol 18L®, which is available from Crompton Corp.;
Witconol GOT®, which is available from Crompton Corp.;
Witconol MST®, which is available from Crompton Corp.; and
Witconol RHT®, which is available from Crompton Cop.;
Glycol Esters, including but not limited to,
Alkamuls 600 DO®, which is available from Rhodia, Inc.;
Alkamuls SEG®, which is available from Rhodia, Inc.;
Atlas EM-2®, which is available from Atlas Refinery Inc.;
Cerasynt P®, which is available from International Specialty Products/IS;
Cerasynt M®, which is available from international Specialty Products/IS;
Cerasynt MN®, which is available from International Specialty Products/IS;
Cerasynt PA®, which is available from international Specialty Products/IS;
Chemsperse EGDS®, which is available from Chemron Corp.;
Chemsperse EGMS®, which is available from Chemron Corp.;
Colonial Monolaurin®, which is available from Colonial Chemical Co.;
DeMuls SGE-95®, which is available from DeForest Enterprises, Inc.;
Eccoterge 200®, which is available from Eastern Color & Chemical Co.;
Emerest 2380®, which is available from Cognis Corporation;
Ethox 2610®, which is available from Ethox Chemicals, LLC;
Ethox DO-9®, which is available from Ethox Chemicals, LLC;
Ethox DO-14®, which is available from Ethox Chemicals, LLC;
Ethox SO-9®, which is available from Ethox Chemicals, LLC;
Fizul MD-318®, which is available from Finetex Inc.;
Genapol EGDS-VHP®, which is available from Clariant Corporation;
Genapol TS Powders®, which is available from Clariant Corporation;
Hostacerin WO®, which is available from Clariant Corporation;
Inversol 140®, which is available from Keil Chemical;
Kemester 104®, which is available from Crompton Corp.;
Kemester 205®, which is available from Crompton Corp.;
Kemester 226®, which is available from Crompton Corp.;
Kemester 5221SE®, which is available from Crompton Corp.;
Kemester EGDS®, which is available from Crompton Corp.;
Lexemul EGDS®, which is available from index Chemical Co.;
Lexemul EGMS®, which is available from Index Chemical Co.;
Lexemul P®, which is available from Inolex Chemical Co.;
Lipo DGLS®, Self-Emulsifying®, which is available from Lipo Chemicals, Inc.;
Lipo EGDS®, which is available from Lipo Chemicals, Inc.;
Lipo PGMS®, which is available from Lipo Chemicals, Inc.;
Liposorb S-4®, which is available from Lipo Chemicals, Inc.;
Liposorb TO-20®, which is available from Lipo Chemicals, Inc.;
Lumulse PGO®, which is available from Lambent Technologies Corp.;
Mackester EGDS®, which is available from The McIntyre Group;
Mackester EGMS®, which is available from The McIntyre Group;
Mackester GSTP®, which is available from The McIntyre Group;
Mackester Series®, which is available from The McIntyre Group;
Magrabar PDG-50®, which is available from Magrabar Chemical Corp.;
Mapeg 6000 DS®, which is available from BASF Corp.;
Marlowet 4702®, which is available from Sasol North America Inc.;
Monalube 305®, which is available from Uniqema;
Monalube 310®, which is available from Uniqema;
Monalube 315®, which is available from Uniqema;
Monalube 320®, which is available from Uniqema;
Monalube 325®, which is available from Uniqema;
Monalube 330®, which is available from Uniqema;
Naturechem PGHS®, which is available from CasChem®, Inc.;
Polycastorol PLO-840®, which is available from Magrabar Chemical Corp.;
Polytex 10M®, which is available from Lipo Chemicals, Inc.;
Ritasynt IP®, which is available from RITA Corp.;
Ross Chem PEG 600 DT®, which is available from Lubrizol Foam Control Additives;
Schercemol PGMS®, which is available from Noveon®, Inc.;
Sponto H-44C®, which is available from Crompton Corp.;
Tegin G®, which is available from Goldschmidt Chemical Corp.;
Witbreak DGE-182®, which is available from Akzo Nobel Surface Chemistry LLC;
Witbreak DGE-182®, which is available from Crompton Corp.;
Witbreak DRA-21®, which is available from Akzo Nobel Surface Chemistry LLC;
Witbreak DRA-21®, which is available from Crompton Corp.;
Witbreak DRA-50®, which is available from Akzo Nobel Surface Chemistry LLC;
Witbreak DRA-50®, which is available from Crompton Corp.;
Witconol F26-46®, which is available from Crompton Corp.;

Witconol H-32®, which is available from Akzo Nobel Surface Chemistry LLC;
Witconol H-33®, which is available from Akio Nobel Surface Chemistry LLC;
Witconol H-35A®, which is available from Crompton Corp.; and
Witconol RHP®, which is available from Crompton Corp.;
Lanolin-based Derivatives, including but not limited to,
Amerchol CAP, which is available from Amerchol Corp.;
Amerchol L-101®, which is available from Amerchol Corp.;
Amerlate LFA-LO®, which is available from Amerchol Corp.;
Amerlate P®, which is available from Amerchol Corp.;
Barre Common Degras®; which is available from RITA Corp.;
Cholesterol NF®, which is available from Croda Inc.;
Crodalan AWS®, which is available from Croda Inc.;
Crodalan LA®, which is available from Croda Inc.;
Emery 1650®, which is available from Cognis Canada Corp.;
Emery 1650®, which is available from Cognis Corporation;
Emery 1740®, which is available from Cognis Canada Corp.;
Emery 1740®; which is available from Cognis Corporation;
Forlan 500®, which is available from RITA Corp.;
Forlan L®, which is available from RITA Corp.;
Laneto 50®, which is available from RITA Corp.;
Laneto 100®, which is available from RITA Corp.;
Laneto AWS®, which is available from RITA Corp.;
Lanfrax 1776®, which is available from Cognis Canada Corp.;
Lanfrax 1776®, which is available from Cognis Corporation;
Lanogel 21®, which is available from Amerchol Corp.;
Lipolan®, which is available from Lipo Chemicals, Inc.;
Lipolan 31®, which is available from Lipo Chemicals; Inc.;
OHlan®, which is available from Amerchol Corp.;
Polychol 5®, which is available from Croda Inc.;
Polychol 15®, which is available from Croda Inc.;
Ritacetyl®, which is available from RITA Corp.;
Ritachol®, which is available from RITA Corp.;
Ritahydrox®, which is available from RITA Corp.;
Ritalafa®, which is available from RITA Corp.;
Ritalan®, which is available from RITA Corp.;
Ritalan AWS®, which is available from RITA Corp.;
Ritalan C®, which is available from RITA Corp.;
Ritawax®, which is available from RITA Corp.;
Ritawax AEO®, which is available from RITA Corp.;
Ritawax ALA®, which is available from RITA Corp.;
Solan/Solan 50/Super Solan®, which is available from Croda Inc.;
Super Hartolan/Hartolan®, which is available from Croda Inc.;
Supersat AWS-4®, which is available from RITA Corp.; and
Supersat AWS-24®, which is available from RITA Corp.;
Lecithin and Lecithin Derivatives, including but not limited to,
Alcolec®, which is available from American Lecithin Co.;
Lecithin®, which is available from Archer Daniels Midland Company:
Lexin K®, which is available from American Lecithin Co.; and
Natipide®, which is available from American Lecithin Co.;
Lignin and Lignin Derivatives, including but not limited to,
Diwatex XP 9®, which is available from Borregaard Lignotech USA Inc.;
Dynasperse LCD®, which is available from Borregaard Lignotech USA Inc.;
Indulin SAL®, which is available from MeadWestvaco Corp.;
Indulin W-1®, which is available from MeadWestvaco Corp.;
Indulin W-5®, which is available from MeadWestvaco Corp.;
Lignosol FTA®, which is available from Borregaard Lignotech USA Inc.;
Lignosol SFX-65®, which is available from Borregaard Lignotech USA Inc.;
Marasperse 52 CP®, which is available from Borregaard Lignotech USA Inc.;
Marasperse AG®, which is available from Borregaard Lignotech USA Inc.;
Marasperse CBOS-4®, which is available from Borregaard Lignotech USA Inc.; and
Ufoxane 2®, which is available from Borregaard Lignotech USA Inc.;
Methyl Esters, including but not limited to,
E.B. Cleaner AK®, which is available from Eastern Color & Chemical Co.;
Oleocal ME-70®, which is available from Lambent Technologies Corp.;
Oleocal ME-92®, which is available from Lambent Technologies Corp.;
Oleocal ME-112®, which is available from Lambent Technologies Corp.; and
Oleocal ME-130®, which is available from Lambent Technologies Corp.;
Monoglycerides and Derivatives, including but not limited to,
Dynacet 211®, which is available from Sasol North America Inc.;
Hetsorb S-20®, which is available from Global-Seven, Inc.;
Imwitor 191®, which is available from Sasol North America Inc.;
Imwitor 370®, which is available from Sasol North America Inc.;
Imwitor 375®, which is available from Sasol North America Inc.;
Imwitor 900®, which is available from Sasol North America Inc.;
Imwitor 945®, which is available from Sasol North America Inc.;
Imwitor 2020®, which is available from Sasol North America Inc.;
Kemester 5500®, which is available from Crompton Corp.;
Kemester 6000®, which is available from Crompton Corp.;
Magrabar GMC®, which is available from Magrabar Chemical Corp.;
Magrabar GMO-CK®, Which is available from Magrabar Chemical Corp.;
Magrabar GPC-10®, which is available from Magrabar Chemical Cop.;
Magrabar MDG-5050®, which is available from Magrabar Chemical Corp.;
Monalube 335®, which is available from Uniqema;
Monoglycerides Glyceryl Monestearate Archer Daniels Midland Company;
Rita GMS®, which is available from RITA Corp.;
Ritamulse SCG®, which is available from RITA Corp.;
Softigen 701®, which is available from Sasol North America Inc.; and
Tally 100 Plus®, which is available from Loders Croklaan U.S.A.;
Polyethylene Glycols, including but not limited to,
Emulgade PL 68/50®, which is available from Cognis Corporation;
Lumulse PEG®, which is available from Lambent Technologies Cop.;
Rhodasurf PEG-400®, which is available from Rhodia, Inc.;

Rhodasurf PEG-600®, which is available from Rhodia, Inc.; and
Witconol PEG-400®, which is available from Akzo Nobel Surface Chemistry LLC;
Polymeric Surfactants, including but not limited to,
Acritamer PNC-EG®, which is available from RITA Corp.;
Ag-Rho DEP-775®, which is available from Rhodia, Inc.;
APG 325N Glycoside®, which is available from Cognis Corporation;
Aristoflex AVC®, which is available from Clariant Corporation;
Aristoflex HMB®, which is available from Clariant Corporation;
Burco NPS-225®, which is available from Burlington Chemical Co.®, Inc.;
Burco NPS-616®, which is available from Burlington Chemical Co.®, Inc.;
Chemccinate 5603®, which is available from Chemron Corp.;
Cosmedia Guar C-261N®, which is available from Cognis Corporation;
Gantrez S-95®, which is available from International Specialty Products/IS;
Glucopon 220 UP®, which is available from Cognis Corporation;
Glucopon 225 DK®, which is available from Cognis Corporation;
Glucopon 425 N®, which is available from Cognis Corporation;
Glucopon 600 UP®, which is available from Cognis Corporation;
Glucopon 625 UP®, which is available from Cognis Corporation;
Pemulen 1621®, which is available from Noveon®, Inc.;
Pemulen 1622®, which is available from Noveon®, Inc.;
Pemulen TR-1®, which is available from Noveon®, Inc.;
Pemulen TR-2®, which is available from Noveon®, Inc.;
Plantacare 818®, which is available from Cognis Corporation;
Plantapon LGC Sorb®, which is available from Cognis Corporation;
Plantaren 1200N®, which is available from Cognis Corporation;
Plantaren 2000N®, which is available from Cognis Corporation;
Viscolam AT 64®, which is available from RITA Corp.;
Viscolam AT 64P®, which is available from RITA Corp.;
Viscolam AT 100®, which is available from RITA Corp.;
Viscolam MAC 7®, which is available from RITA Corp.;
Viscolam SMC 20®, which is available from RITA Corp.;
Witbreak RTC-323®, which is available from Crompton Corp.; and
WSI 3700®, which is available from Jacam Chemicals, L.L.C.;
Propoxylated & Ethoxylated Fatty Acids, Alcohols, or Alkyl Phenols, including but not limited to,
Antarox AA-60®, which is available from Rhoda, Inc.;
Antarox LF-224®, which is available from Rhoda, Inc.;
Burcomul DFE-45®, which is available from Burlington Chemical Co.®, Inc.;
Burcoterge LFE-1000®, which is available from Burlington Chemical Co.®, Inc.;
Chemal LF-25B®, which is available from Chemax Performance Solutions;
Chemal LF-408®, which is available from Chemax Performance Solutions;
Dehypon LS-36®, which is available from Cognis Canada Corp.;
Dehypon LS-36®, which is available from Cognis Corporation;
Dehypon LS-54®, which is available from Cognis Canada Corp.;
Dehypon LS-54®, which is available from Cognis Corporation;
Delonic 100 VLF®, which is available from DeForest Enterprises, Inc.;
Delonic LF-60 MOD®, which is available from DeForest Enterprises, Inc.;
Empiderm B®, which is available from Huntsman LLC;
Ethylan 1206®, which is available from Akzo Nobel Surface Chemistry LLC;
Ethylan NS-500K®, which is available from Akzo Nobel Surface Chemistry LLC;
Ethylan NS-500LQ®, which is available from Akzo Nobel Surface Chemistry LLC;
Genapol 1392®, which is available from Clariant Corporation;
Genapol 2317®, which is available from Clariant Corporation;
Genapol 26EP710®, which is available from Clariant Corporation;
Genapol EP 1022®, which is available from Clariant Corporation;
Genapol EP 1024®, which is available from Clariant Corporation;
Genapol EP 6068®, which is available from Clariant Corporation;
Genapol NP915®, which is available from Clariant Corporation;
Kieralon MFB®, which is available from BASF Corp.;
Lumisolve CSA-80 V®, which is available from Lambent Technologies Corp.;
Marlowet 5001®, which is available from Sasol North America Inc.;
Marlox FK 64®, which is available from Sasol North America Inc.;
Marlox MO 124®, which is available from Sasol North America Inc.;
Marlox S 58®, which is available from Sasol North America Inc.;
Nonatell 1003®, which is available from Tomah Products®, Inc.;
Nonatell 1038®, which is available from Tomah Products®, Inc.;
Nonatell 1052®, which is available from Tomah Products®, Inc.;
Nonatell 1061®, which is available from Tomah Products®, Inc.;
Nonatell 1075®, which is available from Tomah Products®, Inc.;
Nonatell 1088®, which is available from Tomah Products®, Inc.;
Nonatell 1123®, which is available from Tomah Products®, Inc.;
Nonatell 1153®, which is available from Tomah Products®, Inc.;
Nonatell 1161®, which is available from Tomah Products®, Inc.;
Nonatell 1172®, which is available from Tomah Products®, Inc.;
Nonatell 1181®, which is available from Tomah Products®, Inc.;
Norfox 36®, which is available from Norman, Fox & Co.;

Procetyl AWS®, which is available from Croda Inc.;
Sandoxylate SX 412® Liquid, which is available from Clariant Corporation;
Sandoxylate SX 418®, which is available from Clariant Corporation;
Surfonic JL-80X®, which is available from Huntsman LLC;
Surfonic JL-80X-B1®, which is available from Huntsman LLC;
Surfonic L4-29X®, which is available from Huntsman LLC;
Surfonic LP®, which is available from Huntsman LLC;
T-Det A826®, which is available from Harcros Chemicals Inc.;
T-Det LF-416®, which is available from Harcros Chemicals Inc.;
Tergitol Min-Foam 1X®, which is available from Dow Chemical Company;
Tergitol Min-Foam 2X®, which is available from Dow Chemical Company;
Triton CF-21®, which is available from Dow Chemical Company;
Triton CF-76®, which is available from Dow Chemical Company;
Triton XL-80N®, which is available from Dow Chemical Company;
Witconol NS-98®, which is available from Akzo Nobel Surface Chemistry LLC;
Witconol NS-108LQ®, which is available from Akzo Nobel Surface Chemistry LLC;
Witconol NS-145®, which is available from Akzo Nobel Surface Chemistry LLC; and
Witconol NS-179®, which is available from Akzo Nobel Surface Chemistry LLC;
Protein-based Surfactants, including but not limited to,
AminoFoam W®, which is available from Croda Inc.;
Amiter LGOD-2®, which is available from Ajinomoto USA, Inc.;
Amiter LGS-2®, which is available from Ajinomoto USA, Inc.;
Amiter LGS-5®, which is available from Ajinomoto USA, Inc.;
Lamepon S®, which is available from Cognis Canada Corp.;
Lamepon which is available from Cognis Corporation;
Maypon 4C®, which is available from Inolex Chemical Co.;
May-Tein C®, which is available from Maybrook, Inc.;
May-Tein CT®, which is available from Maybrook, Inc.;
May-Tein KTS®, which is available from Maybrook, Inc.;
May-Tein SY®, which is available from Maybrook, Inc.;
Plantapon S®, which is available from Cognis Corporation;
Proteol APL®, which is available from Seppic Inc.;
Proteol OAT®, which is available from Seppic Inc.;
Pyroter CPI-40®, which is available from Ajinomoto USA, Inc.;
Pyroter GPI-25®, which is available from Ajinomoto USA, Inc.;
Supro-Tein S®, which is available from Maybrook, Inc.; and
Supro-Tein V®, which is available from Maybrook, Inc.;
Sarcosine Derivatives, including but not limited to,
Crodasinic LS-30®, which is available from Croda Inc.;
Vanseal CS®, which is available from R. T. Vanderbilt Co. Inc.;
Vanseal LS®, which is available from R. T. Vanderbilt Co. Inc.;
Vanseal MS®, which is available from R. T. Vanderbilt Co. Inc.;
Vanseal NACS-30®, which is available from R. T. Vanderbilt Co. Inc.;
Vanseal NALS-95®, which is available from R. T. Vanderbilt Co. Inc.; and
Vanseal OS®, which is available from R. T. Vanderbilt Co. Inc.;
Silicone-based Surfactants, including but not limited to,
Abil-B-9950®, which is available from Goldschmidt Chemical Corp.;
Abil Care 85®, which is available from Goldschmidt Chemical Corp.;
Abil EM 90®, which is available from Goldschmidt Chemical Corp.;
Abil EM 97®, which is available from Goldschmidt Chemical Corp.;
Abil WE-09®, which is available from Goldschmidt Chemical Corp.;
Dow Coming 1248 Fluid®, which is available from Dow Coming Corp.;
Dow Coming 3225C® Formulation Aid, which is available from Dow Coming Corp.;
Dow Coming 5200® Formulation Aid, which is available from Dow Coming Corp.;
Dow Coming Q4-3667® Fluid, which is available from Dow Coming Corp.;
Monasil PCA®, which is available from Uniqema;
Monasil PDM®, which is available from Uniqema;
Monasil PLN®, which is available from Uniqema;
Polyderm PPI-SI-WS®, which is available from Alzo International, Inc.;
Troysol 380W®, which is available from Troy Corporation; and
Troysol S366®, which is available from Troy Corporation;
Sorbitan Derivatives, including but not limited to,
Alkamuls SML®, which is available from Rhodia, Inc.;
Alkamuls SMO®, which is available from Rhodia, Inc.;
Alkamuls STO®, which is available from Rhodia, Inc.;
Arlacel 20®, which is available from Uniqema;
Arlacel 40®, which is available from Uniqema;
Arlacel 60®, which is available from Uniqema;
Arlacel 80®, which is available from Uniqema;
Arlacel C®, which is available from Uniqema;
Armul 21®, which is available from Crompton Corp.;
Atlox 80®, which is available from Uniqema;
Atlox 847®, which is available from Uniqema;
Atlox 1045A®, which is available from Uniqema;
Canarcel 20®, which is available from Canamex Quimicos S.A de C.v;
Canarcel 60®, which is available from Canamex Quimicos S.A de C.v;
Canarcel 80®, which is available from Canamex Quimicos S.A de C.v;
Canarcel TW 20®, which is available from Canamex Quimicos S.A de C.v;
Canarcel TW 60®, which is available from Canamex Quimicos S.A de C.v;
Canarcel TW 80®, which is available from Canamex Quimicos S.A de C.v;
Coladet BSB-P®, which is available from Colonial Chemical Co.;
Customulse O-20®, which is available from Custom Ingredients, Inc.;
Dehymuls E®, which is available from Cognis Canada Corp.;
DeSotan SMO®, which is available from Crompton Corp.;
DeSotan SMO-20®, which is available from Crompton Corp.;
DeSotan SMT®, which is available from Crompton Corp.;
DeSotan SMT-20®, which is available from Crompton Corp.;

Durfax 60®, which is available from Loders. Croklaan U.S.A.;
Durfax 65®, which is available from Loders Croklaan U.S.A.;
Durfax 80®, which is available from Loders Croklaan U.S.A.;
Durtan 60®, which is available from Loders Croklaan U.S.A.;
Durtan 65®, which is available from Loders Croklaan U.S.A.;
Liposorb L®, which is available from Lipo Chemicals, Inc.;
Liposorb L-10®, which is available from Lipo Chemicals, Inc.;
Liposorb L-20®, which is available from Lipo Chemicals, Inc.;
Liposorb O®, which is available from Lipo Chemicals, Inc.;
Liposorb O-20®, which is available from Lipo Chemicals, Inc.;
Liposorb P®, which is available from Lipo Chemicals, Inc.;
Liposorb P-20®, which is available from Lipo Chemicals, Inc.;
Liposorb S®, which is available from Lipo Chemicals, Inc.;
Liposorb S-20®, which is available from Lipo Chemicals, Inc.;
Liposorb SQO®, which is available from Lipo Chemicals, Inc.;
Liposorb TO®, which is available from Lipo Chemicals, Inc.;
Liposorb TS®, which is available from Lion Chemicals, Inc.;
Liposorb TS-20®, which is available from Lipo Chemicals, Inc.;
Lumisorb PS®, which is available from Lambent Technologies Corp.;
Lumisorb SMO (T)®, which is available from Lambent Technologies Corp.;
Lumisorb SMS K®, which is available from Lambent Technologies Corp.;
Lumisorb SSO®, which is available from Lambent Technologies Corp.;
Lumisorb STS K®, which is available from Lambent Technologies Corp.;
Lumisorb STT®, which is available from Lambent Technologies Corp.;
Magrabar SMO®, which is available from Magrabar Chemical Corp.;
Magrabar SMO-VEG®, which is available from Magrabar Chemical Corp.;
Magrabar SMT®, which is available from Magrabar Chemical Corp.;
Magrabar STO®, which is available from Magrabar Chemical Corp.;
Miracare BC-27®, which is available from Rhodia, Inc.;
Ritabate 20®, which is available from RITA Corp.;
Ritabate 40®, which is available from RITA Corp.;
Ritabate 60®, which is available from RITA Corp.;
Ritabate 80®, which is available from RITA Corp.;
T-Maz®, which is available from BASF Corp.;
Tego SML®, which is available from Goldschmidt Chemical Corp.;
Tego SML 20®, which is available from Goldschmidt Chemical Corp.;
Tego SMO 80 V®, which is available from Goldschmidt Chemical Corp.;
Tego SMO V®, which is available from Goldschmidt Chemical Corp.;
Tego SMS®, which is available from Goldschmidt Chemical Corp.;
Tego STO V®, which is available from Goldschmidt Chemical Corp.;
Tween 21®, which is available from Uniqema;
Tween 40®, which is available from Uniqema;
Tween 60®, which is available from Uniqema;
Tween 60 K®, which is available from Uniqema;
Tween 61®, which is available from Uniqema;
Tween 65®, which is available from Uniqema;
Tween 80®, which is available from Uniqema;
Tween 80 K®, which is available from Uniqema;
Tween 81®, which is available from Uniqema; and
Tween 85®, which is available from Uniqema;
Sucrose and Glucose Esters and Derivatives, including but not limited to,
DeSulf GOS-P-60WCG®, which is available from DeForest Enterprises, Inc.;
Glucam E-20 Distearate®, which is available from Amerchol Corp.;
Glucamate DOE-120®, which is available from Amerchol Corp.;
Glucamate SSE-20®, which is available from Amerchol Corp.;
Glucate DO®, which is available from Amerchol Corp.;
Glucate SS®, which is available from Amerchol Corp.;
Glucopon 425 UP®, which is available from Cognis Corporation;
Isolan IS®, which is available from Goldschmidt Chemical Corp.;
Mazon 40®, which is available from BASF Corp.;
Montanov 82®, which is available from Seppic Inc.;
Montanov 202®, which is available from Seppic Inc.;
Montanov S®, which is available from Seppic Inc.;
Rheozan®, which is available from Rhodia, Inc.;
Simulsol AS 48®, which is available from Seppic Inc.;
Simulsol SL 4®, which is available from Seppic Inc.;
Simulsol SL 10®, which is available from Seppic Inc.;
Simulsol 11W®, which is available from Seppic Inc.;
Simulsol SL 55®, which is available from Seppic Inc.:
Suga Nate 100 and 160®, which is available from Colonial Chemical Co.;
Tego Care 450®, which is available from Goldschmidt Chemical Corp.;
Tego Care CG 90®, which is available from Goldschmidt Chemical Corp.;
Tego Care PS®, which is available from Goldschmidt Chemical Corp.;
Tegosoft PSE 141 G®, which is available from Goldschmidt Chemical Corp.;
Tegotens G 826®, which is available from Goldschmidt Chemical Corp.;
Triton BG-10 (70%)®, which is available from Dow Chemical Company;
Triton CG-110 (60%)®, which is available from Dow Chemical Company; and
Wickenol 545®, which is available from Alzo International, Inc.

Pluronic from BASF is another useful type of surfactant.

Another embodiment comprises from about 0.001% to about 0.1% cyclosporin A, castor oil, and a sorbitan ester.

Another embodiment comprises from about 0.001% to about 0.1% cyclosporin A, castor oil, and Polysorbate 20.

Another embodiment comprises from about 0.001% to about 0.1% cyclosporin A, castor oil, and Polysorbate 40.

Another embodiment comprises from about 0.001% to about 0.1% cyclosporin A, castor oil, and Polysorbate 60.

Another embodiment comprises from about 0.001% to about 0.1% cyclosporin A, castor oil, and Polysorbate 80.

Another embodiment comprises from about 0.001% to about 0.1% cyclosporin A, castor oil, and a stearate.

Another embodiment comprises from about 0.001% to about 0.1% cyclosporin A, castor oil, and glyceryl stearate.

Another embodiment comprises from about 0.001% to about 0.1% cyclosporin A, castor oil, and isopropyl stearate.

Another embodiment comprises from about 0.001% to about 0.1% cyclosporin A, castor oil, and polyoxyl stearate.

Another embodiment comprises from about 0.001% to about 0.1% cyclosporin A, castor oil, and propylene glycol stearate.

Another embodiment comprises from about 0.001% to about 0.1% cyclosporin A, castor oil, and sucrose stearate.

Another embodiment comprises from about 0.001% to about 0.1% cyclosporin A, castor oil, and polyethylene glycol.

Another embodiment comprises from about 0.001% to about 0.1% cyclosporin A, castor oil, and polyethylene oxide.

Another embodiment comprises from about 0.001% to about 0.1% cyclosporin A, castor oil, and polypropylene oxide.

Another embodiment comprises from about 0.001% to about 0.1% cyclosporin A, castor oil, and a polyethylene oxide-polypropylene oxide copolymer.

Another embodiment comprises from about 0.001% to about 0.1% cyclosporin A, castor oil, and an alcohol ethoxylate.

Another embodiment comprises from about 0.001% to about 0.1% cyclosporin A, castor oil, and an alkylphenol ethoxylate.

Another embodiment comprises from about 0.001% to about 0.1% cyclosporin A, castor oil, and an alkyl glycoside.

Another embodiment comprises from about 0.001% to about 0.1% cyclosporin A, castor oil, and alkyl polyglycoside.

Another embodiment comprises from about 0.001% to about 0.1% cyclosporin A, castor oil, and a fatty alcohol.

Another embodiment comprises from about 0.001% to about 0.1% cyclosporin A, castor oil, and hydroxypropylmethyl cellulose.

Another embodiment comprises from about 0.001% to about 0.1% cyclosporin A, castor oil, and carboxymethyl cellulose.

Another embodiment comprises from about 0.001% to about 0.1% cyclosporin A, castor oil, and a polyacrylic acid.

Another embodiment comprises from about 0.001% to about 0.1% cyclosporin A, castor oil, and a Carbomer.

Another embodiment comprises from about 0.001% to about 0.1% cyclosporin A, castor oil, and a phosphalipid.

Another embodiment comprises from about 0.001% to about 0.1% cyclosporin A, castor oil, and phosphatidyl chioline.

Another embodiment comprises from about 0.001% to about 0.1% cyclosporin A, castor oil, and phosphatidyl serine.

Another embodiment comprises from about 0.005% to about 0.05% cyclosporin A, castor oil, and a sorbitan ester.

Another embodiment comprises from about 0.005% to about 0.05% cyclosporin A, castor oil, and Polysorbate 20.

Another embodiment comprises from about 0.005% to about 0.05% cyclosporin A, castor oil, and Polysorbate 40.

Another embodiment comprises from about 0.005% to about 0.05% cyclosporin A, castor oil, and Polysorbate 60.

Another embodiment comprises from about 0.005% to about 0.05% cyclosporin A, castor oil, and Polysorbate 80.

Another embodiment comprises from about 0.005% to about 0.05% cyclosporin A, castor oil, and a stearate.

Another embodiment comprises from about 0.005% to about 0.05% cyclosporin A, castor oil, and glyceryl stearate.

Another embodiment comprises from about 0.005% to about 0.05% cyclosporin A, castor oil, and isopropyl stearate.

Another embodiment comprises from about 0.005% to about 0.05% cyclosporin A, castor oil, and polyoxyl stearate.

Another embodiment comprises from about 0.005% to about 0.05% cyclosporin A, castor oil, and propylene glycol stearate.

Another embodiment comprises from about 0.005% to about 0.05% cyclosporin A, castor oil, and sucrose stearate.

Another embodiment comprises from about 0.005% to about 0.05% cyclosporin A, castor oil, and polyethylene glycol.

Another embodiment comprises from about 0.005% to about 0.05% cyclosporin A, castor oil, and polyethylene oxide.

Another embodiment comprises from about 0.005% to about 0.05% cyclosporin A, castor oil, and polypropylene oxide.

Another embodiment comprises from about 0.005% to about 0.05% cyclosporin A, castor oil, and a polyethylene oxide-polypropylene oxide copolymer.

Another embodiment comprises from about 0.005% to about 0.05% cyclosporin A, castor oil, and an alcohol ethoxylate.

Another embodiment comprises from about 0.005% to about 0.05% cyclosporin A, castor oil, and an alkylphenol ethoxylate.

Another embodiment comprises from about 0.005% to about 0.05% cyclosporin A, castor oil, and an alkyl glycoside.

Another embodiment comprises from about 0.005% to about 0.05% cyclosporin A, castor oil, and alkyl polyglycoside.

Another embodiment comprises from about 0.005% to about 0.05% cyclosporin A, castor oil, and a fatty alcohol.

Another embodiment comprises from about 0.005% to about 0.05% cyclosporin A, castor oil, and hydroxypropylmethyl cellulose.

Another embodiment comprises from about 0.005% to about 0.05% cyclosporin A, castor oil, and carboxymethyl cellulose.

Another embodiment comprises from about 0.005% to about 0.05% cyclosporin A, castor oil, and a polyacrylic acid, Another embodiment comprises from about 0.005% to about 0.05% cyclosporin A, castor oil, and a Carbomer.

Another embodiment comprises from about 0.005% to about 0.05% cyclosporin A, castor oil, and a phosphalipid.

Another embodiment comprises from about 0.005% to about 0.05% cyclosporin A, castor oil, and phosphatidyl chioline.

Another embodiment comprises from about 0.005% to about 0.05% cyclosporin A, castor oil, and phosphatidyl serine.

Another embodiment comprises about 0.05% cyclosporin A, castor oil, and a sorbitan ester.

Another embodiment comprises about 0.05% cyclosporin A, castor oil, and Polysorbate 20.

Another embodiment comprises about 0.05% cyclosporin A, castor oil, and Polysorbate 40.

Another embodiment comprises about 0.05% cyclosporin A, castor oil, and Polysorbate 60.

Another embodiment comprises about 0.05% cyclosporin A, castor oil, and Polysorbate 80.

Another embodiment comprises about 0.05% cyclosporin A, castor oil, and a stearate.

Another embodiment comprises about 0.05% cyclosporin A, castor oil, and glyceryl stearate.

Another embodiment comprises about 0.05% cyclosporin A, castor oil, and isopropyl stearate.

Another embodiment comprises about 0.05% cyclosporin A, castor oil, and polyoxyl stearate.

Another embodiment comprises about 0.05% cyclosporin A, castor oil, and propylene glycol stearate.

Another embodiment comprises about 0.05% cyclosporin A, castor oil, and sucrose stearate.

Another embodiment comprises about 0.05% cyclosporin A, castor oil, and polyethylene glycol.

Another embodiment comprises about 0.05% cyclosporin A, castor oil, and polyethylene oxide.

Another embodiment comprises about 0.05% cyclosporin A, castor oil, and polypropylene oxide.

Another embodiment comprises about 0.05% cyclosporin A, castor oil, and a polyethylene oxide-polypropylene oxide copolymer.

Another embodiment comprises about 0.05% cyclosporin A, castor oil, and an alcohol ethoxylate.

Another embodiment comprises about 0.05% cyclosporin A, castor oil, and an alkylphenol ethoxylate.

Another embodiment comprises about 0.05% cyclosporin A, castor oil, and an alkyl glycoside.

Another embodiment comprises about 0.05% cyclosporin A, castor oil, and alkyl polyglycoside.

Another embodiment comprises about 0.05% cyclosporin A, castor oil, and a fatty alcohol.

Another embodiment comprises about 0.05% cyclosporin A, castor oil, and hydroxypropylmethyl cellulose.

Another embodiment comprises about 0.05% cyclosporin A, castor oil, and carboxymethyl cellulose.

Another embodiment comprises about 0.05% cyclosporin A, castor oil, and a polyacrylic acid.

Another embodiment comprises about 0.05% cyclosporin A, castor oil, and a Carbomer.

Another embodiment comprises about 0.05% cyclosporin A, castor oil, and a phosphalipid.

Another embodiment comprises about 0.05% cyclosporin A, castor oil, and phosphatidyl chloline, Another embodiment comprises about 0.05% cyclosporin A, castor oil, and phosphatidyl serine.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

In accordance with the present invention, the emulsions can be further stabilized using a polyelectrolyte, or polyelectrolytes if more than one, from the family of cross-linked polyacrylates, such as carbomers and Pemulen®.

Pemulen® is a registered trademark of S. F. Goodrich for polymeric emulsifiers and commercially available from B.F. Goodrich Company, Specialty Polymers & Chemicals Division, Cleveland, Ohio. Pemulens are Acrylates/C10-30 Alkyl Acrylate Cross-Polymers. They are high molecular weight co-polymers of acrylic acid and a long chain alkyl methacrylate cross-linked with allyl ethers of pentaerythritol. They contain not less than 52.0 percent and not more than 62.0 percent of carboxylic acid groups. The viscosity of a neutralized 1.0 percent aqueous dispersion is between 9,500 and 26,500 centipoises.

In addition, the tonicity of the emulsions can be further adjusted using glycerine, mannitol, or sorbitol if desired. The pH of the emulsions can be adjusted in a conventional manner using sodium hydroxide to a near physiological pH level and while buffering agents are not required, suitable buffers may include phosphates, citrates, acetates and borates.

Examples of useful formulations are shown below.

| Ingredients | 1 | 2 | 3 | 4 | 5 |
| --- | --- | --- | --- | --- | --- |
| Cyclosporine A (% w/w) | 0.1 | 0.1 | 0.08 | 0.03 | 0.08 |
| Castor oil (% w/w) | 1.00 | 1.2 | 0.50 | 0.50 | 0.50 |
| Clove oil (% w/w) | 0.70 | | | | |
| Cassia oil (% w/w) | | 0.4 | 0.55 | | |
| Olive oil (% w/w) | | | 0.35 | | |
| Mineral Oil (% w/w) | | | | | 0.80 |
| Polysorbate-80 (% w/w) | 1.00 | 0.80 | | 0.30 | |
| Diglycerol (% w/w) | 0.70 | | 0.20 | | 0.80 |
| Polyglycerol-3 (% w/w) | | | | | |
| Simulsol OX 1005L (% w/w) | | 0.60 | | | |
| Brij78 (% w/w) | | | 1.20 | | |
| Glycerin (% w/w) | 2.00 | 1.70 | 2.00 | 2.00 | 2.00 |
| CMC (% w/w) | 0.50 | | 0.50 | | |
| Pemulen TR-2 (% w/w) | | 0.05 | | 0.02 | |
| Purified Water | QS | QS | QS | QS | QS |
| Sodium Hydroxide | pH adj | pH adj | pH adj | pH adj | pH adj |
| pH | 7.2 | 7.5 | 7.1 | 6.8 | 7.4 |

Another useful emulsion consists of the following: 0.1% cyclosporin A, 0.20% castor oil, 0.75% polyethylene oxide 40 stearate (Myrj 52 ®), 0.2% Polysrobate 80, 1.0% glycerin, 0.6% boric acid, 0.5% carboxymethylcellulose, 100 ppm stabilized oxychloro complex (Purite ®), sufficient sodium hydroxide to adjust the pH, and the remainder water, wherein the pH is from 7.3 to 7.5.

Unless otherwise indicated, all indications of % in the specification or the claims herein, or in any priority applications incorporated by reference herein, are intended to mean % (weigh/weight).

Although there has been hereinabove described a particular pharmaceutical composition in the form of a nonirritating emulsion for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

The invention claimed is:

1. An ophthalmically acceptable emulsion comprising 0.1% cyclosporin A, castor oil, lecithin, Polysorbate 80, Pemulen, and a cellulose derivative selected from the group consisting of hydroxypropylmethyl cellulose and carboxymethyl cellulose.

* * * * *